(12) United States Patent
Törnkvist et al.

(10) Patent No.: US 9,103,932 B2
(45) Date of Patent: Aug. 11, 2015

(54) METHOD, APPARATUS, AND SYSTEM FOR EXAMINING OPTICALLY A SAMPLE CARRIED IN A PLURALITY OF WELLS

(75) Inventors: Niklas Törnkvist, Kauniainen (FI); Pekka Hänninen, Turku (FI)

(73) Assignee: Aqsens Oy, Espoo (FI)

( * ) Notice: Subject to any disclaimer, the term of this patent is extended or adjusted under 35 U.S.C. 154(b) by 0 days.

(21) Appl. No.: 13/877,266

(22) PCT Filed: Sep. 30, 2011

(86) PCT No.: PCT/FI2011/050848
§ 371 (c)(1),
(2), (4) Date: Jul. 2, 2013

(87) PCT Pub. No.: WO2012/042118
PCT Pub. Date: Apr. 5, 2012

(65) Prior Publication Data
US 2013/0277545 A1    Oct. 24, 2013

(30) Foreign Application Priority Data
Oct. 1, 2010    (EP) .................................... 10185942

(51) Int. Cl.
*G01V 8/20* (2006.01)
*G01N 21/64* (2006.01)

(52) U.S. Cl.
CPC .............. *G01V 8/20* (2013.01); *G01N 21/6408* (2013.01); *G01N 21/6452* (2013.01); *G01N 21/6454* (2013.01); *G01N 2201/0626* (2013.01); *G01N 2201/129* (2013.01)

(58) Field of Classification Search
CPC .............. G01N 21/64; G01N 21/6428; G01N 21/6456; G01N 21/6458
USPC .................................. 250/461.1, 462.1, 459.1
See application file for complete search history.

(56) References Cited

U.S. PATENT DOCUMENTS

| 6,542,241 | B1 | 4/2003 | Thorwirth et al. |
| 6,545,758 | B1* | 4/2003 | Sandstrom ..................... 356/317 |
| 2003/0016352 | A1* | 1/2003 | Goldman et al. ............. 356/317 |
| 2004/0043502 | A1 | 3/2004 | Song et al. |
| 2005/0052652 | A1* | 3/2005 | Filippini et al. .............. 356/434 |
| 2006/0055042 | A1 | 3/2006 | Klapproth et al. |

(Continued)

FOREIGN PATENT DOCUMENTS

| WO | WO 02/099397 A2 | 12/2002 |
| WO | WO 03/067936 A1 | 8/2003 |
| WO | WO 2008/002267 A1 | 1/2008 |

(Continued)

*Primary Examiner* — David Porta
*Assistant Examiner* — Djura Malevic
(74) *Attorney, Agent, or Firm* — Patterson Thuente Pedersen, P.A.

(57) ABSTRACT

An apparatus and method are disclosed for examining optically a sample carried in a plurality of wells. A holder is adapted to receive and hold in place a sample carrier. A plurality of excitation means selectively introduce excitation towards a spatially limited portion of a sample carrier held in place by said holder. Detecting means receive and detect emission radiation coupled out from a light output window of a sample carrier held in place by said holder. Said detecting means is common to said excitation means and is configured to receive emission radiation from a plurality of different spatially limited portions of a sample carrier held in place by said holder.

21 Claims, 5 Drawing Sheets

(56) References Cited

U.S. PATENT DOCUMENTS

2008/0316571 A1* 12/2008 MacAulay ............... 359/239
2009/0017477 A1* 1/2009 Harma et al. ............ 435/7.72

FOREIGN PATENT DOCUMENTS

| WO | WO 2009/027102 A2 | 3/2009 |
| WO | WO 2011/031377 A1 | 3/2011 |

* cited by examiner

| SAMPLE | NSS1 | NSS2 | NSS3 | NSS4 | NSS5 | NSS6 | PCA1 | PCA2 |
|---|---|---|---|---|---|---|---|---|
| tap water | 135028 | 100191 | 97515 | 133278 | 142444 | 197635 | 322909 | 197744 |
| tap water | 132253 | 89262 | 96286 | 132785 | 131120 | 192290 | 311140 | 195287 |
| tap water | 127494 | 93170 | 79366 | 77106 | 144898 | 206883 | 290190 | 202298 |
| bottle water 1 | 36687 | 23040 | 29142 | 29770 | 39839 | 72347 | 117861 | 100527 |
| bottle water 1 | 37022 | 22712 | 28520 | 31077 | 39081 | 76200 | 118605 | 104765 |
| bottle water 1 | 37820 | 22702 | 30770 | 24967 | 28375 | 72356 | 112325 | 99091 |
| bottle water 2 | 31662 | 33044 | 28494 | 29488 | 24451 | 25001 | 103856 | 52259 |
| bottle water 2 | 24447 | 24697 | 16228 | 29204 | 22052 | 24211 | 91493 | 56977 |
| bottle water 2 | 24497 | 26927 | 16628 | 26600 | 23979 | 29584 | 93369 | 61294 |
| bottle water 3 | 98039 | 72162 | 47990 | 64171 | 50148 | 16057 | 176215 | 25253 |
| bottle water 3 | 100369 | 78786 | 89642 | 14549 | 51134 | 17156 | 177223 | 6306 |
| bottle water 3 | 97280 | 78301 | 77233 | 45018 | 49190 | 17229 | 182255 | 15670 |
| bottle water 4 | 9114 | 4795 | 4552 | 6824 | 6479 | 27009 | 58107 | 64682 |
| bottle water 4 | 6701 | 6718 | 4472 | 5745 | 6966 | 31522 | 58545 | 69093 |
| bottle water 4 | 5928 | 3963 | 4556 | 6268 | 5919 | 33151 | 57284 | 71515 |
| bottle water 5 | 59126 | 57958 | 62247 | 29069 | 62070 | 56182 | 159424 | 66130 |
| bottle water 5 | 63854 | 70343 | 65064 | 26931 | 67657 | 55194 | 168578 | 60728 |
| bottle water 5 | 75713 | 63260 | 65905 | 50488 | 65038 | 53078 | 178777 | 62200 |
| bottle water 6 | 20875 | 12138 | 18969 | 18919 | 20559 | 90360 | 94656 | 123747 |
| bottle water 6 | 16527 | 11586 | 16668 | 12303 | 16717 | 77477 | 85016 | 110981 |
| bottle water 6 | 17569 | 11302 | 15984 | 16351 | 14951 | 110153 | 92493 | 144452 |

METHOD, APPARATUS, AND SYSTEM FOR EXAMINING OPTICALLY A SAMPLE CARRIED IN A PLURALITY OF WELLS

PRIORITY CLAIM

This application is a National Phase entry of PCT Application No. PCT/FI2011/050848, filed Sep. 30, 2011, which claims priority from EP Application No. 10185942.9, filed Oct. 1, 2010, the disclosures of which are hereby incorporated by referenced herein in their entirety.

TECHNICAL FIELD OF THE INVENTION

The present invention relates to a method, apparatus, and system for examining optically a sample carried in a plurality of spots or wells. Especially the present invention relates to a reading method and apparatus for reading a stick- or slide-like device comprising multiple spots or wells having interacting surfaces and utilizing luminophore labels, especially fluorescent labels. In addition the present invention relates to a computer program product for reading the device and for characterizing and/or determining a sample.

BACKGROUND OF THE INVENTION

Solutions for characterising samples by reading luminescent labels are known from prior art. A typical prior art solution has a light-emitting means for emitting excitation radiation having a first wavelength which is suitable for exciting a luminophore label, whereafter the excited luminophore material radiates emission radiation having a second wavelength characteristic to said luminophore material. The emission radiation is then detected by detection means. The excitation may be introduced also in the form of electric current or electric field, or a chemical reactant. In these cases the terms electroluminescence and chemiluminescence are used respectively.

One challenge related to prior art solutions is to distinguish the radiation used for excitation from the radiation emitted by the excited label and especially to detect only emission radiation. There are solutions that utilise monochromators to select and distinguish the wavelengths used for excitation radiation from the radiation emitted by luminophore labels. Another way is to employ time-resolved methods, as is described in US 2004/043502 A1, where the reader utilizes a pulsed excitation source and a time-gated detector with suitable control logic for measuring the intensity of the emission radiation.

Still another solution is described in US 2006/0055042, where a radiation source is located outside a measurement chamber where the sample is injected. The excitation radiation is injected through a semiconductor substrate into the internal cavity of the measurement chamber. For the detection of the luminescent radiation emitted by the luminescent substance, a plurality of radiation receivers are located on the semiconductor substrate with their detection side facing the internal cavity of the measurement chamber.

A further challenge related to prior art solutions is their inherently complicated structure and consequently high cost of manufacturing and operating, as well as the requirement of laboratory conditions. The use of monochromators, arrays of radiation receivers, scanning (confocal) detection, and/or time-gated detectors with suitable controlling logic tends to make the system complex and expensive and in addition vulnerable to malfunctions. The same is true concerning stepping motors and the like that move the sample holder to achieve reading of the wells. One should aim at developing a simple, robust, and low cost reader that is capable of sensitively recording and distinguishing the emission radiation from a plurality of sample wells or array spots, and that can be deployed even in harsh real-life environments.

SUMMARY OF THE INVENTION

An objective of the present invention is to alleviate and eliminate the problems and disadvantages relating to prior art solutions. One objective is to introduce a method and an apparatus for examining optically a sample carried in a plurality of spots or wells so that the apparatus can be made structurally simple and the components of the apparatus can be minimized. Another objective is to make it possible to read a device comprising multiple spots or wells with luminophore labels so that the excitation radiation would not disturb the detection of the emission radiation of said luminophore labels. Yet another objective is to provide a structural solution that makes the apparatus robust, resistant to environmental interfering factors, and simple to manufacture and operate.

The objectives of the present invention can be achieved by the features of the independent claims.

In some aspects, the present invention relates to a method for examining optically a sample carried in a plurality of wells, the method comprising receiving a sample carrier in a holder and holding said sample carrier in place, selectively introducing excitation from an excitation means subgroup towards at least two of the wells of said sample carrier, where said excitation means subgroup comprises at least two excitation means, and receiving and detecting emission radiation coupled out from said at least two of the wells of said sample carrier, wherein said receiving and detecting is performed commonly to said excitation means subgroup by receiving and detecting emission radiation with a common detector from a plurality of different spatially limited portions of said sample carrier.

In some aspects, the present invention relates to an apparatus for examining optically a sample carried in a plurality of wells, the apparatus comprising a holder adapted to receive and hold in place a sample carrier, an excitation means subgroup adapted to selectively introduce excitation towards at least two of the wells said sample carrier held in place by said holder, where said excitation means subgroup comprises at least two excitation means, and detecting means for receiving and detecting emission radiation coupled out from said at least two of the wells of said sample carrier held in place by said holder, wherein said detecting means is common to said excitation means subgroup and is configured to receive emission radiation from a plurality of different spatially limited portions of said sample carrier held in place by said holder.

In some aspects, the present invention relates to a computer program product comprising machine-readable instructions that, when executed by a processor, are configured to cause the processor to implement a method, the method comprising as a response to an indication of a sample carrier being held in place by a holder, selectively introducing excitation from an excitation means subgroup towards at least two of the wells of said sample carrier, where said excitation means subgroup comprises at least two excitation means, and receiving and detecting emission radiation coupled out from said at least two of the wells of said sample carrier, wherein said receiving and detecting is performed commonly to said excitation means subgroup by receiving and detecting emission radiation with a common detector from a plurality of different spatially limited portions of said sample carrier.

In order to enable considering an advantageous configuration for the apparatus, we assume that a sample will be carried by a sample carrier that comprises a plurality of spots or wells. The sample carrier is received in and held in place by a holder. Excitation means are used to selectively introduce excitation towards a desired portion of the sample carrier. In other words, selected ones of said spots or wells are excited at a time. A detecting means is used to receive and detect emission radiation coupled out from a light output window of the sample carrier. The detecting means is common to said radiating means, so that it is configured to receive emission radiation from a plurality of different spatially limited portions of the sample carrier either simultaneously or in sequence.

The excitation means may be radiating excitation means, which are adapted to radiate excitation radiation on at least one wavelength that is suitable for exciting luminophore labels that appear on the sample carrier together with the sample. If it is possible that the sample carrier comprises a plurality of luminophore labels having different excitation wavelengths, radiating excitation means providing two or more different wavelengths are advantageously used. This can be accomplished either by employing fixed-wavelength radiation sources of different kinds, or by employing at least one radiation source that has a controllable output wavelength.

According to an embodiment of the present invention the excitation means may comprise electric excitation means configured to trigger electroluminescence, and/or chemical excitation means configured to trigger chemiluminescence.

The sample carrier is assumed to comprise a plurality of (reaction) spots or wells with interacting surfaces, where the sample to be determined is introduced. At least a portion of the spots or wells may comprise an interacting surface for the purpose of interacting with the sample, luminophore label, and/or combination of the sample and said label. It should be noted that the luminophore label may be introduced to the spots or wells beforehand, at the same time with, or after the sample. Again it should be noted that the sample is advantageously introduced in liquid form, either as such or appropriately diluted in a dilution medium, optionally comprising at least one labelling reactant with a luminophore label. After introducing said sample to the spots or wells the sample is allowed to react with the interacting surfaces, such as binding surfaces.

The excitation radiation is advantageously radiated by one or more of said plurality of radiating excitation means to the spots or wells, or at least to portions of the spots or wells, of the device for exciting luminophore labels in the spots or wells. Excitation radiation may be radiated by switching on predetermined subgroups of the available radiating excitation means. Most advantageously a number of predetermined subgroups of the available radiating excitation means are switched on in sequence, so that each subgroup comprises at least one radiating excitation means and at most as many as there are available radiating excitation means. After excitation each of the excited luminophore label will return to its ground state and emit characteristic emission radiation with a certain wavelength which is detected by the detecting means. One of the advantages of the present invention is that the detection of all emission peaks (even from all spots or wells) can be implemented by using only one detecting means, such as photomultiplier tube, CCD device or the like. Of course two or more detecting means can also be employed but there is no need to dedicate an individual detector for certain well or wells. However, advantageously there is only one detecting means, which is in addition common for all the radiating means.

Keeping the number of detecting means small (or even equal to one) is advantageous, because this helps to reduce the overall manufacturing cost of the apparatus. Additionally it helps to avoid problems that could otherwise result from individual differences between different detector components. Another advantage is the achievable increase in signal to noise ratio, because one detector can now receive a signal from more than one spot or well simultaneously (if simultaneous irradiation of more than one spot or well is used), and thus a larger number of meaningful quanta are available for detection.

The sample carrier may itself have an optical function, which means that some part of the sample carrier collects emission radiation from the spots or wells and directs it towards an output window defined by the sample carrier. In that case the apparatus should comprise an emission radiation input window, which is configured to match the emission radiation output window defined by the sample carrier when the sample carrier is held properly in place by the holder. As an example, the output window may be located at an edge of a plate-like form of the sample carrier, in which case the emission radiation input window must be located at a place where the corresponding edge of the sample carrier will appear.

One advantage of the present invention is that no part of the apparatus or sample carrier needs to be moved during a measurement. In other words, the excitation means and the detecting means are stationary, and also the holder may keep the sample carrier stationary after it has been received into the appropriate location for measurement. This helps to keep the mechanical structure simple and reliable.

According to an embodiment the excitation means are radiating excitation means implemented advantageously by LEDs, such as UV-radiating LEDs, or laser, for example, but also other suitable radiating means known by the skilled person can be applied. Also a light source with a plurality of optical fibers can be used, in which case the plurality of radiating excitation means is to be understood to mean the output ends of the optical fibers. An optical controller is then needed for controlling the delivery of excitation radiation to the desired spots or wells via said optical fibers. It is to be noted that also any combination of the different excitation radiation sources can be used. As an example there can be an individual radiating excitation means for each spot or well of the device to be read, such as for example 2-100, advantageously 5-50, and more advantageously 10-30 radiating excitation means. There can be more radiating excitation means than there are spots or wells, and the invention is anyhow not limited to the numbers of the radiating excitation means or spots or wells of the device to be read.

According to an advantageous embodiment each of the radiating excitation means or a group comprising at least two radiating excitation means can be controlled individually. The radiating excitation means can be controlled for example so that a) only one radiating excitation means is active at a time, b) at least two radiating excitation means are active at a time, c) a predetermined subgroup of all radiating excitation means are active at a time, or d) all radiating excitation means are active at a time. The radiating excitation means can be operated in any combination of active and non-active radiating excitation means by controlling said radiating excitation means to be active or inactive for example by separately and independently flashing them, so in other words to multiplex the radiating excitation means and detection means. This allows measuring any combination of the spots or wells with luminophore materials.

It should be noted that the present invention allows a sample to be characterized by a single "result", which is understood to mean information that relates an executed sequence of excitation pulses—possibly involving different subgroups of the excitation means—to the received and detected emission radiation. In other words, there are predetermined some combinations of the excitation means to be activated simultaneously, as well as the sequential order of such combinations. Activating only one excitation means is considered a limiting case of the concept "combination". The detection of the emission peaks induced by said activated subgroups of excitation means determines the result and a characteristic "fingerprint" of the sample. According to an embodiment the emission radiation is measured in a time-resolved manner. An exemplary time window during which the emission radiation is detected is for example 100-1000 µs, or 200-800 µs after the excitation pulse. The time window depends on the characteristics of the used luminophore labels.

According to an embodiment each of the active excitation means or combinations of them, such as their identification information (comprising e.g. location in relation to the spots or wells of the device to be read, wavelength, intensity, polarization, and exposure, as an example) and the corresponding output of the detecting means describing the intensity of the emission peak are registered to obtain information in which spots or wells (or interacting surfaces comprised by said spots or wells) the luminophore labels are bound and how intensively, i.e. the amount of the labels bound. Using and analysing the registered information a fingerprint of the sample can be achieved, so in other words the sample can be characterized and/or determined by comparing said fingerprint of the sample with i) at least one fingerprint of at least one corresponding sample, ii) at least one fingerprint of an array obtained without a sample, and/or iii) at least one fingerprint of known samples.

The luminophore label means in this document any suitable label substance or compound, which can be used in the device of the invention. The luminophore label comprises a luminophore, i.e. a fluorophore or phosphor, or other luminescent material, which can be excited with a specific optical, chemical and/or electrical excitation signal and which re-emits energy at a specific wavelength that in the case of optical excitation is different than the excitation wavelengths and has preferably a relatively long emission lifetime (at least nanoseconds, but even several hundreds of microseconds depending on the material used). As an example the luminophore label may be selected from the group comprising coumarins, rhodamines, cyanines, boron-dipyrromethenes, lanthanide compounds, preferably chelates and cryptates, porphyrins, metalloporphyrins, fluorescent proteins, fluorescent polymers, particulate labels, preferably quantum dots, luminescent crystals and luminescent polymer particles, and any combination thereof. It should be noted that also two or more luminophore labels may be used in determination of the sample either simultaneously or in sequence.

Typically an optically excitable luminophore label exhibits a difference of at least several tens of nanometers (Stokes shift) between the most effectively absorbed excitation wavelength and the characteristic emission wavelength, whereupon it is easy to detect and whereupon the emission peak is easier to determine in relation to excitation wavelength. As an example the luminophore in the luminophore label may be europium, samarium, terbium, and/or dysprosium. It should be noted that the invention is however not limited only to those substances mentioned.

According to an embodiment the luminophore is selected such that it is luminescent or shows delayed fluorescence or phosphorescence upon excitation with suitable wavelength light. The luminophore may also be a combination or a mixture of a fluorescent substance and a substance exhibiting delayed luminescence upon excitation with light of suitable wavelength.

DEFINITIONS

In this disclosure, the term "sample carrier" refers to a device that comprises a plurality of different interacting surfaces, such as binding surfaces. These are typically located in a regular array of cavities known as sample wells, reaction wells, or just wells. They may also be located within spots on a flat surface of the sample carrier. Typically not all interacting surfaces of the device, i.e. elements of the spots or wells, are identical. However, the sample carrier can, and in many preferred embodiments does, comprise, in addition to a plurality of different interacting surfaces, also one or more mutually similar interacting surfaces.

The term luminophore label refers to a label that comprises a luminophore, i.e. inorganic or organic luminescent matter.

The term luminophore refers to an atom, group or particulate, i.e. of a luminophore label, that manifests luminescence and detection of the label accordingly consists of measuring the luminescence of the luminophore. Luminophores comprise e.g. of fluorophores, phosphors, but also conjugated pi systems and transition metal complexes. Luminophores preferred in embodiments of the present invention can be selected from the group consisting of coumarins, rhodamines, cyanines, boron-dipyrromethenes, lanthanide compounds (such as chelates and cryptates), porphyrins, metalloporphyrins, fluorescent proteins, fluorescent polymers, particulate labels (such as quantum dots, luminescent crystals and luminescent polymer particles). Luminophore may also be understood as a complex that is formed of a luminescent molecule or particle as defined above and non-luminescent molecules or molecular complexes.

The term "fingerprint" refers, in this context, to a series, an array, and/or a matrix of results obtained through detection, i.e. measurement, of the plurality of different interacting surfaces of the sample carrier measured in any embodiment of the invention. If a sample carrier is known to involve a plurality of identical interacting surfaces and more than one of these are detected, the fingerprint can comprise all the results of the identical interacting surfaces or alternatively only a representative value, e.g. average, median, mode of the measurements of identical interacting surfaces or any combination thereof. A fingerprint can further refer to a profile of measured luminescent intensities subjected to numerical processing with an appropriate algorithm. In many embodiments of the invention, the measured luminescent intensities of the interacting surfaces of the device are subjected to numerical processing by an appropriate algorithm before comparison with fingerprints of corresponding devices without a sample and/or known samples.

The terms "corresponding sample" and "corresponding samples" refer to samples that are believed to be virtually identical, highly similar or at least reasonably similar to those characterized and/or determined. This belief of similarity can be due to e.g. origin, i.e. relating to the same or a corresponding process or product, or classification.

The term "known samples" refers to any samples which composition is known in detail or is fully characterized.

The terms "non-specific interacting means" or "non-specific binder" refer e.g. to a binder or binders that are, in the context of a specific embodiment of the present invention, not specific: the selectivity of the binding is not predetermined. Accordingly a binder, which in some other context is a specific binder, might, in the context of the present invention be a non-specific binder due to that binding in the context of the present invention is not specific. Preferably the non-specific binder or binders of the present invention are not specific binders in any context.

The terms "specific interacting means" or "specific binder" refer e.g. to a binder that is specific or binders that are specific. A specific binder comprises a molecular recognition element or elements that bind to an epitope of the analyte bound. In the context of this invention a specific binder only binds to similar epitopes, i.e. epitopes that are chemically and structurally similar. A specific binder does not bind to more than 10, preferably not more than 3, chemically and conformationally non-identical different epitopes. Most preferably a specific binder only binds to one specific epitope.

In the context of the present invention the term "to bind" refers to binding wherein the binding constant is at least $10^3$ $M^{-1}$, preferably at least $10^5$ $M^{-1}$, more preferably at least $10^7$ $M^{-1}$ and most preferably at least $10^9$ $M^{-1}$.

The exemplary embodiments of the present invention presented in this document are not to be interpreted to pose limitations to the applicability of the appended claims. The verb "to comprise" is used in this document as an open limitation that does not exclude the existence of also unrecited features. The features recited in depending claims are mutually freely combinable unless otherwise explicitly stated.

BRIEF DESCRIPTION OF THE DRAWINGS

Next the present invention will be described in greater detail with reference to exemplary embodiments in accordance with the accompanying drawings, in which.

DETAILED DESCRIPTION OF THE DRAWINGS

Figure 1:
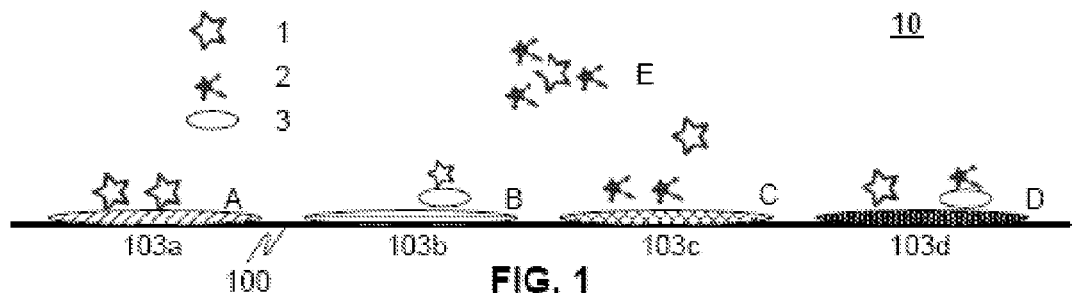
FIG. 1 illustrates a principle of an exemplary method for characterizing and/or determining a sample according to an advantageous embodiment.

FIG. 1 illustrates a principle 10 of an exemplary method for characterizing and/or determining a sample (2, 3) with a sample carrier 100 comprising multiple wells 103 employing at least two different interacting surfaces 103a, 103b, 103c, 103d and utilising luminophore labels (1), especially fluorescent labels. The surface spots marked with A, B, C, D represent differently coated or modified surfaces each forming a differently behaving non-specific interacting surface. The sample molecules (2, 3) may interact with the surfaces in different ways. In A the sample molecules do not react with the spots and only the label (1) will bind to the surface. In B the sample molecule reacts with both label (1) and surface bringing the label (1) in contact with the spot. In this case the label (1) does not bind to the non-specific component B. In C the sample molecules (2) prevent the binding of the label (1) to the surface. In D both sample molecules (2,3) and label bind to the surface. In E the sample molecules (2) bind to the label molecule (1) inhibiting the molecule to interact with any of the surface spots (A,B,C,D). In this example each of the surfaces has different type of the optically readable properties due to different interactions with the samples and/or label, whereupon a specific fingerprint can be determined for each case, as is additionally depicted in FIG. 2.

Figure 2:
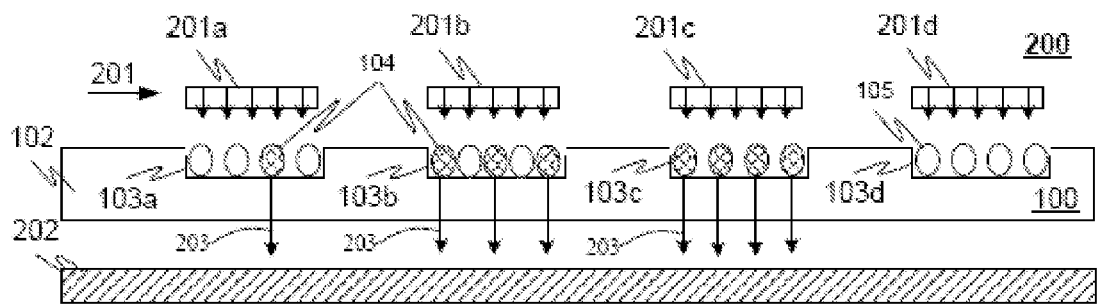
FIG. 2 illustrates a principle of an exemplary apparatus for reading a device for characterizing and/or determining a sample according to an exemplary embodiment of the present invention.

FIG. 2 illustrates a principle of an exemplary apparatus 200 for reading a sample carrier 100 for characterizing and/or determining a sample according to an exemplary embodiment of the invention. The apparatus comprises a plurality of radiating means 201 (separately referred to as 201a, 201b, 201c, 201d) adapted to radiate excitation radiation to at least portions of the wells 103a, 103b, 103c, 103d of the sample carrier 100 for exciting luminophore labels 104. In addition the apparatus 200 comprises also a detecting means 202 for detecting emission radiation 203 emitted by the excited luminophore label 104. It should be noted that according to an advantageous embodiment the detecting means 202 is common for all radiating means 201.

The concept of having a detecting means common for excitation means can be characterized in various ways. One way is to say that the number of individual detecting means in the apparatus is smaller than the number of individual (and individually controllable) excitation means. This numerical relationship implies that the same detecting means must be used for at least two different excitation means. Another possible characterisation is thus to say that the apparatus is configured to utilize the same detecting means in association with the activation of at least two different excitation means. Yet another possible characterisation is to assume that at least a majority of the individual excitation means are disposed to correspond with a regular array of sample wells in a sample carrier held in place by the holder, and that the detecting means is configured to collect emission radiation from a plurality of such sample wells. The detecting means do not even need to have any direct spatial relationship with the sample wells, because at least in some embodiments of the invention the sample carrier may have an optical function, so that it collects and directs emission radiation from a plurality of wells into a direction that points at the detecting means, when the sample carrier is held in place.

As the FIG. 2 describes as an example, the different kinds of interacting surfaces of wells 103a, 103b, 103c, and 103d have interacted and bound the sample 105 (white ovals, as in well 103d), at least one labelling reactant 104 (striped oval, as in well 103c), and/or combination of the sample and at least one labelling reactant in different ways, as in wells 103a, 103b (at least portion of the wells have bound them non-specifically). Thus, when the wells having different amounts of the bound samples or labelling reactants are exposed to the excitation radiation to excite the bound luminophore labels, different intensities of luminescence are detected depending on the amount of the luminophore labels, as is illustrated by different numbers of the emission arrows 203.

For example only one unit of photons are counted from well 103a as the luminescent label 104 does not bind very well to the interacting surface of well 103a. However, three units of photons are counted from well 103b because the luminescent labels and sample molecules 105 bind equally to the interacting surface of well 103b. Moreover, four units of photons are counted from well 103c as the luminescent label binds much better to the interacting substrate of well 103c than the sample. As an example, no photons are counted from well 103d as the sample binds much better to the interacting surface of well 103d than the luminescent label. The situation would be the same (no photons), if neither sample molecules nor labels do interact with the interacting surface of the well, as was the case for example with spot E in FIG. 1.

There are also other phenomena that may influence the emission from the sample wells (A,B,C,D). The sample may e.g. interact with the luminophore in a way that the emission from the luminophore may is enhanced or quenched. The enhancement or quenching may happen on the nonspecifically binding surface or in the solution. Several theoretical reasons for the enhancement or quenching can be found in prior art and can be considered known to persons skilled in the field of luminescence.

Figure 3A:
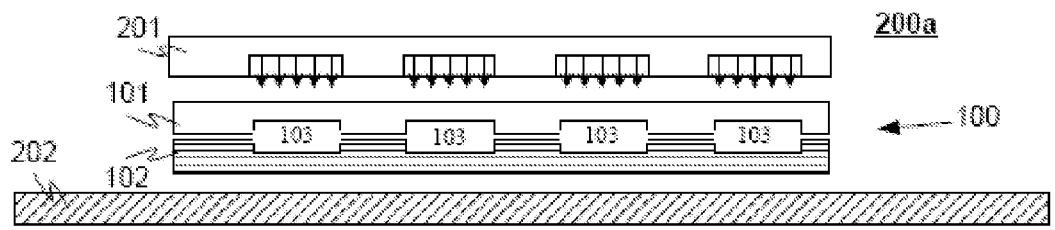
FIG. 3A illustrates a schematic view of an exemplary apparatus according to an advantageous embodiment of the present invention.

FIG. 3A illustrates a schematic view of an exemplary apparatus 200a according to an advantageous embodiment of the invention, where the apparatus is adapted to receive the sample holder 100 to be read essentially between the detecting means 202 and a plurality of radiating means 201. The device 100 may be inserted between the means 201 and 202 so, that at least portion of the wells 103 of the sample carrier 100 are between said means 201, 202, and so that especially at least the wells the labels of which are to be excited and measured are between said means 201, 202. Especially the sample carrier 100 is arranged optically between the means 201, 202. The term "optically between" means here that the excitation radiation does not enter directly or freely into the detecting means 202, but hits the wells of the sample carrier 100 and that the emission radiation is derived somehow into the detection means from the wells.

The apparatus 200a is especially suitable for reading the sample carrier 100, where the sample carrier comprises a layer 102, which is essentially (optically) non-transparent for the excitation radiation used, but essentially (optically) transparent for the emission radiation of the excited luminophore labels. Thus the excitation radiation does not disturb the detection, because it is filtered by the second layer 102. There is no need for special monochromators, and basically there would be little need for time-gated detectors either. The device may comprise at least one layer 101, which is essentially (optically) transparent for an excitation radiation radiated by the radiating means 201.

Despite the excitation-filtering function of the layer 102, it may be advantageous to introduce time-gating to the detection of emission radiation. One reason is that the layer 102 may not manage to block all excitation radiation, some of which might then enter the detector and become misinterpreted as emission radiation. It is also possible that some short-lived autofluorescence in the sample (or some other involved material, like the structural materials of the sample carrier) takes place during and immediately after the excitation radiation pulse, which should not be confused with the desired emission radiation from the luminophore label(s). Autofluorescence decays typically much faster than the emission radiation from luminiphore labels, so it can be avoided by time-gated detection. Yet another possible reason to use time-gated detection is the possibility of measuring the emission radiation during two or more different time intervals of a single emission period, which gives information about the decaying rate and lifetime of the emission radiation.

Additionally the Rayleigh and Raman scattering of the excitation radiation must be taken into account. Raman scattering involves a Stokes shift due to the inelastic scattering mechanism, and is thus susceptible of introducing interference to such fluorometric measurements where the detector is active simultaneously with the introduction of optical excitation. It is believed that Raman scattering will set an absolute limit of about $10^{-10}$ M to the sensitivity of simultaneous fluorometric measurements unless sophisticated techniques from e.g. single molecule detection are used.

Figure 3B:
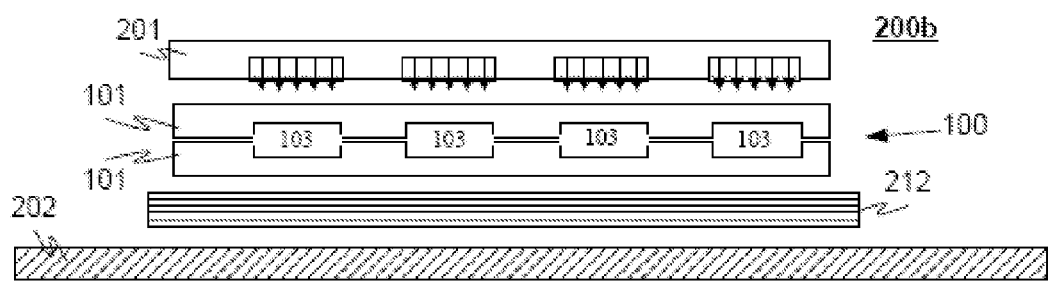
FIG. 3B illustrates a schematic view of another exemplary apparatus according to an advantageous embodiment of the present invention.

FIG. 3B illustrates further schematic view of another exemplary apparatus 200b according to an advantageous embodiment of the invention, where the apparatus 200b is otherwise similar than the device 200a depicted in FIG. 3A, but the apparatus 200b comprises an additional layer 212. The layer 212 is advantageously arranged between the detecting means 202 and a plurality of the radiating means 201 and in addition so that the sample carrier 100 to be read is arranged to be inserted between said radiating means 201 and said layer 212. Layer 212 has a similar task as layer 102 in the sample carrier 100 of FIG. 3A, so that it is essentially (optically) non-transparent for the excitation radiation used, but essentially (optically) transparent for the emission radiation of the excited luminophore labels. The material, constitution, and dimensions of layer 212 can be chosen based on the label material and on the wavelength of the emission peak of the labels. In addition the layer 212 may comprise different areas (corresponding different wells employing e.g. different labels with different emission characters) so that a first area may be transparent for a different wavelength than a second area of the layer 212.

The apparatus 200b is suitable also for reading sample carriers that do not comprise the second layer 102 illustrated in FIG. 3A for blocking the excitation radiation. However, it should be noted that the apparatus 200b can also be used in connection with sample carriers employing the second layer 102.

A common feature to the embodiments of the invention illustrated in FIGS. 2, 3A, and 3B is the assumption that the emission radiation output window of the sample carrier is planar and located on that side of the sample carrier that faces downwards in the Figures. Light will be coupled out of such a relatively large, planar emission radiation output window as a distribution of rays that originate from each sample well where emission occurs, and propagate from such well into a hemisphere of directions under the well. In order to detect as many of such rays as possible, it is advantageous to have the detecting means comprise an emission radiation input window that matches the emission radiation output window, i.e. that covers at least the same planar area as the lower surface of the sample carrier held in place by the holder.

The area covered by the emission radiation input window does not need to be the same as the cross-sectional area of an actual detector. From the technology of optical instruments it is known that optical radiation collected from a wider area may be concentrated onto a smaller area by using light guides, fiber optics, or other corresponding solutions.

Figure 3C:
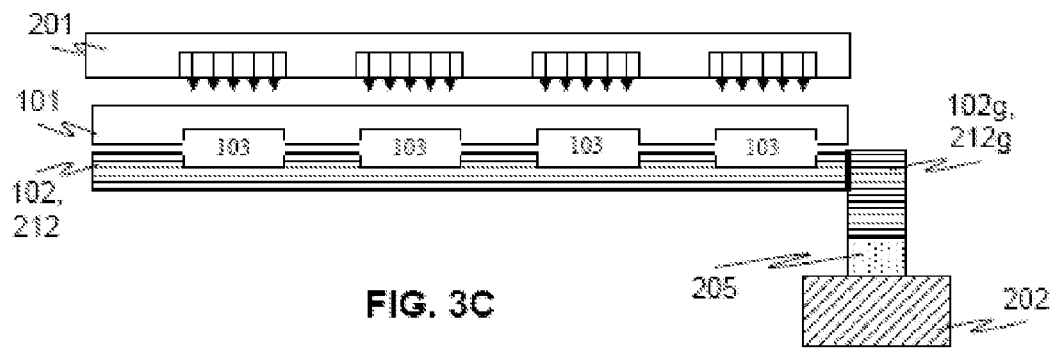
FIG. 3C illustrates a schematic view of still another exemplary apparatus according to an advantageous embodiment of the present invention.

The layer 102 of the sample carrier 100 (or the layer 212 of the apparatus for reading said sample carrier according to any of the embodiment described in this document) may comprise or be arranged to function also as a light guide. FIG. 3C illustrates schematically a solution where a layer 102 of the sample carrier is basically planar and at least partly defines the wells 103. At one edge of its generally planar form the sample carrier comprises light guiding means 102g, into which the emission radiation will be collected by using the light guiding properties of the layer 102 as a whole. Collecting and directing the emission radiation into the appropriate direction may be enhanced by using reflective coatings on the other surfaces of the layer 102. In this exemplary embodiment the light guiding means 102g even change the propagation direction of the collected emission radiation, so that an emission radiation output window is in this case a relatively small slit at the lower edge of the light guiding means 102g.

Another possible interpretation of FIG. 3C is that the light guiding means is a part of the reader apparatus, for which reason it is also illustrated with reference designator 212g in FIG. 3C. According to that interpretation the emission radiation output window of the sample carrier is at the rightmost edge of layer 102 in FIG. 3C, and the emission radiation input window of the apparatus is the surface of the light guiding means 212g that comes against said edge when the sample carrier is held in place by the holder.

The examples of FIGS. 2, 3A, 3B, and 3C show that the invention allows relatively much freedom in designing the apparatus so that its emission radiation input window will be configured to match an emission radiation output window defined by a sample carrier held in place by the holder. Basically the holder and its immediate surroundings delimit an empty space that the sample carrier will essentially fill, and one of the surfaces delimiting said empty space in the apparatus constitutes the emission radiation input window.

Another feature illustrated in FIG. 3C is the provision of one or more optical filters 205 for additionally filtering possible unwanted wavelength(s) from the radiation guided by the light guiding means 102g, 212g. According to an embodiment the filter means 205 can be controlled to transmit or block certain wavelengths, for example if two or more luminophore labels with different emission characters are used.

Figure 4A:
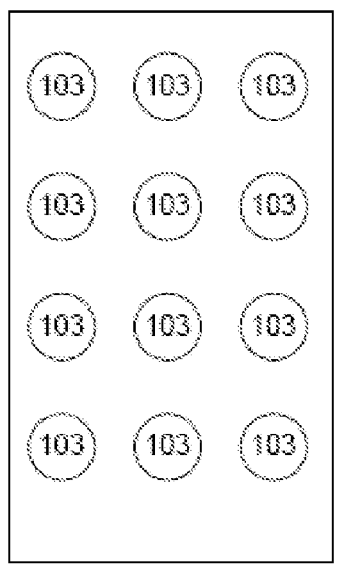
FIG. 4A illustrates a schematic view of wells of an exemplary device according to an advantageous embodiment of the present invention.
Figure 4B:
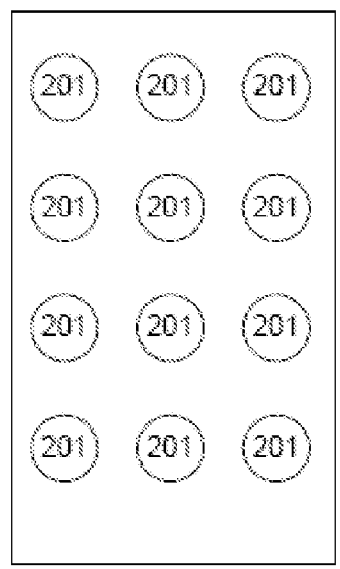
FIG. 4B illustrates a schematic view of placing of radiating means of an exemplary apparatus according to an advantageous embodiment of the present invention.

FIG. 4A illustrates a schematic view of wells 103 of an exemplary device according to an advantageous embodiment of the invention, where the sample and the luminophore labels are to be introduced. FIG. 4B illustrates a schematic view of the location of radiating excitation means 201 in an exemplary apparatus according to an advantageous embodiment of the invention. Advantageously the radiating excitation means 201 are arranged so that each of them will correspond with a certain well 103 of the device when said device is placed into the apparatus for reading. The apparatus advantageously comprises individual radiating excitation means for example 2-100, more advantageously 5-50, and still more advantageously 10-30 wells depending on the devices to be read by said apparatus. It is to be noted that there can be more radiating excitation means in the apparatus than the wells in the device to be read.

Figure 4C:
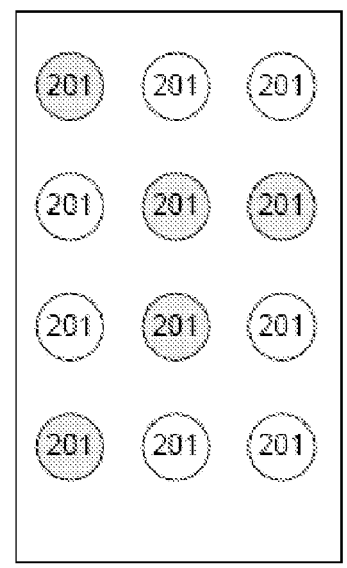
FIG. 4C illustrates a schematic view of active and non-active radiating means of an exemplary apparatus according to an advantageous embodiment of the present invention.

FIG. 4C illustrates a schematic view of active (grey spots) and non-active (white spots) radiating excitation means 201 of an exemplary apparatus according to an advantageous embodiment of the invention, where only the active radiating excitation means 201 radiates excitation radiation to the corresponding wells 103 of the device to be read. According to an advantageous embodiment each of the radiating excitation means 201 or a group comprising at least two radiating excitation means can be controlled individually so that any combination of the active and non-active radiating excitation means 201 can be performed by controlling the radiating excitation means to be active or inactive for example by separately and independently flashing (multiplexing) them as is discussed elsewhere in this document. For example when determining whether a sample comprises a certain molecule(s), a certain combination of the active radiating excitation means is enough to determining the sample or the fingerprint of the molecule(s), because it is know that said certain molecule(s) to be detected bind(s) to particular well(s) of the device (characteristic fingerprint for said molecule).

Spatially limiting the excitation radiation emitted by an individual radiation source deserves some consideration. The use of detecting means that are common to a plurality of excitation radiation sources relies on the assumption that crosstalk between excitation radiation sources remains under control; i.e. crosstalk either does not exist to any significant extent or that crosstalk only exists where it is known and meant to exist. An effective way to reduce crosstalk is to use highly directional sources of excitation radiation, such as LEDs, lasers, or output ends of optical fibers. Their directionality can be further enhanced with collimators and/or lenses, which may be part of the apparatus or which may in some cases be implemented as parts of the sample carrier. An advantageous structure of a sample carrier is such where the body that defines the wells is made of a material (such as polycarbonate) that is non-transparent to the excitation radiation. That side of the sample carrier from which the excitation radiation comes may then be either completely open or comprise only a thin cover layer of a material (such as polymethylmethacrylate) that is transparent to the excitation radiation.

Crosstalk-limiting measures to be taken in the design of that part of the apparatus that houses the excitation radiation sources may include, but are not limited to, using as small and inherently as directional radiation sources as possible, separating adjacent radiation sources with walls that are non-transparent to excitation radiation, and minimising the distance between the excitation radiation sources and the nearest surface of a sample carrier held in place by the holder.

Figure 5:
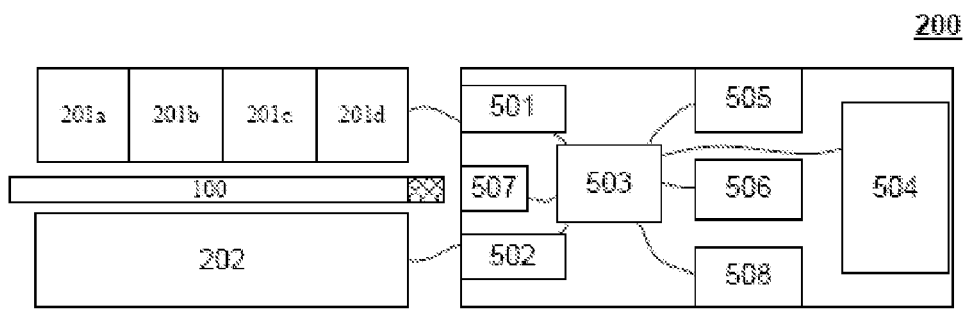
FIG. 5 illustrates a schematic view of an exemplary apparatus according to an advantageous embodiment of the present invention.

FIG. 5 illustrates a schematic view of an exemplary apparatus 200 according to an advantageous embodiment of the invention. The apparatus comprises a plurality of radiating excitation means 201, such as LEDs, for example UV-radiating LEDs, or laser or a light source with a plurality of optical fibers, and a detecting means 202, such as a photomultiplier tube or a semiconducting detector (like CCD or CMOS) sensitive to the emission radiation emitted by the excited luminophore labels that are likely to be used on a sample carrier 100.

The apparatus 200 also comprises an excitation radiation controller 501 for controlling any combination of the radiating excitation means 201 of the device 100 to be active or non-active at a certain time and possibly with a certain wavelength, as is discussed elsewhere in this document. The excitation radiation controller 501 may also determine other information related to each of the radiating excitation means 201, such as the wavelength intensity, polarity, exposure and the locations of radiating excitation means in relation to the wells of the device so that the excited wells can be determined, for example. In addition the apparatus also comprises controlling means 502 for controlling the reading of the detecting means 202 such as determining the emission radiation at a predetermined moment or period of time after exciting at least one of the wells. The controlling means 501 and 502 may be controlled (multiplexed) by a master controller 503 so that any combination of the wells of the device read can be registered with determined information, such as intensities corresponding excited and read wells as well as labels used, if labels with different emission wavelength are used.

In addition the apparatus 200 may comprise a user interface 504 for example for operating said apparatus and possible also for displaying the determined data, such as a fingerprint of the sample as an example. The user interface means may be ON/OFF type means, but also additional functions can be integrated, such as functionality for determining whether the sample to be read comprises a certain molecule or other substance.

The apparatus may also comprise a memory means 505 comprising for example a library of fingerprints of samples, and processor means 506 for determining a fingerprint of the sample. The apparatus can obtain the fingerprint and thereby characterize and/or determine the sample for example by comparing the fingerprint of the sample with i) at least one fingerprint of at least one corresponding sample, ii) at least one fingerprint of an array obtained without a sample, and/or iii) at least one fingerprint of known samples, where the comparison can be performed by the processor means 506.

In addition the apparatus may comprise an identification reader 507 for detecting and identifying the sample carrier to be read. The sample carrier 100 may comprise identification means, whereupon the identification reader 507 can identify the device and couple the measured data of the device for example in the data library to a certain device or its identification information for later use. The identification can be implemented e.g. by RFID means or barcodes for example, whereupon the identification reader 507 is a RFID reader or barcode reader, correspondingly. Also other type means can be employed known by the skilled person. For example the type of the used sample carrier 100 and the used labels as well as other information can be determined via the identification information of the device for example from the data library comprising information of the used devices.

The apparatus may also comprise data communication means 508 for transferring data between the apparatus and an outer data communication means, such as data networks, servers, databases, data computing centres and data libraries comprising information in relation to samples, molecules and their fingerprints, for example. The apparatus may for example send the determined data (such as measured intensities of the wells of the device, as well as identification information of the sample carrier) to the outer data computing centre and afterwards receive the analysed data to be displayed to the user, such as a fingerprint or plain information whether the sample comprises a certain molecule or other substance. Thus the analysis functions can be performed in and all the profiles of the samples (such as liquids) can be performed in a centralized (cloud-based) database, for example.

Figure 6A:
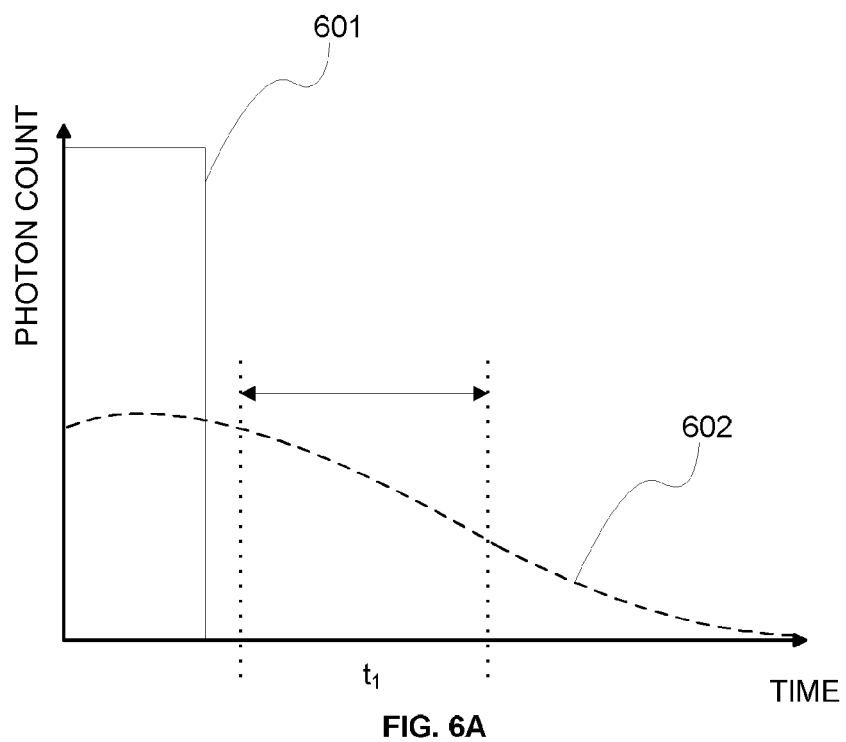
FIG. 6A illustrates an exemplary principle of the method for utilising time-resolved measurement according to an exemplary embodiment of the present invention.
Figure 6B:
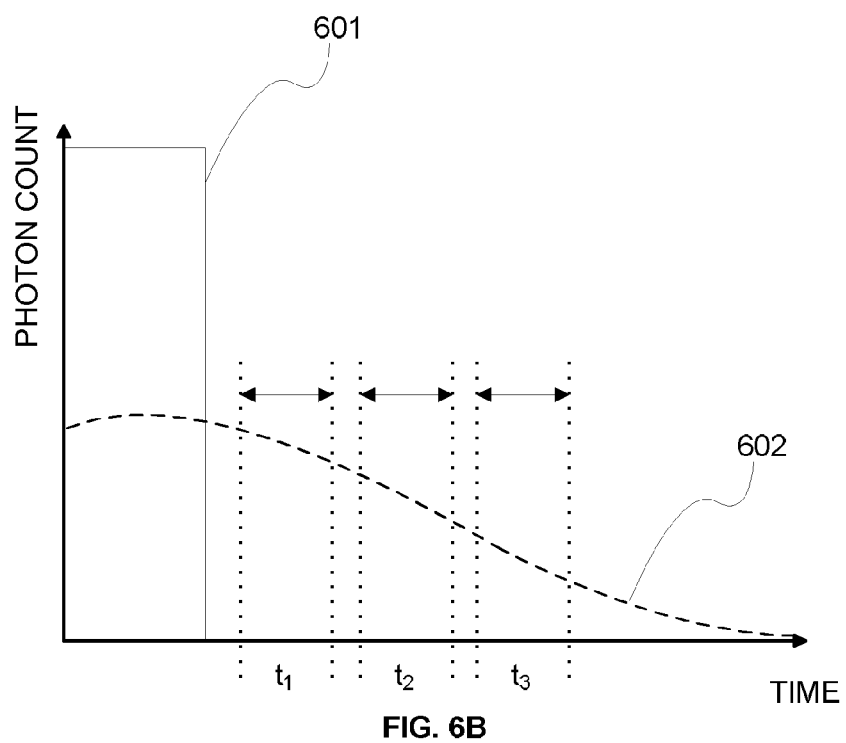
FIG. 6B illustrates another exemplary principle of the method for utilising time-resolved measurement according to an exemplary embodiment of the present invention.

FIGS. 6A and 6B illustrates exemplary principles of the method for utilising time-resolved measurements according to an exemplary embodiment of the invention, where an excitation pulse 601 is emitted to a predetermined subgroup of the wells of the sample carrier. The excitation pulse (as well as any background radiation) is short-living (typically less than 100 µs), whereas the emission peak of the excited luminophore label is long-living (typically some hundreds of microseconds). The emission radiation 602 is advantageously measured after the excitation radiation and any background radiation have typically decayed already, such as during 200-800 µs ($t_1$) after the excitation pulse. According to another embodiment the excitation radiation 602 can be determined in a plurality of parts ($t_1$, $t_2$, $t_3$), whereupon the attenuation of the emission can also be determined possibly describing a character of the label/sample.

An advantageous method for processing the raw fingerprint data (the count of luminescent photons obtained from each specific reading of the detector(s)) is principal component analysis or PCA. As a mathematical procedure PCA transforms a number of variables, among which some mutual correlation may occur, into a smaller number of uncorrelated variables. The output values of PCA are called principal components. PCA is not the only possible processing method; numerous other methods are known and can be applied to derive characteristic descriptors of a group of values so that the number of said characteristic descriptors is smaller than the original number of said values.

Figures 7, 8:
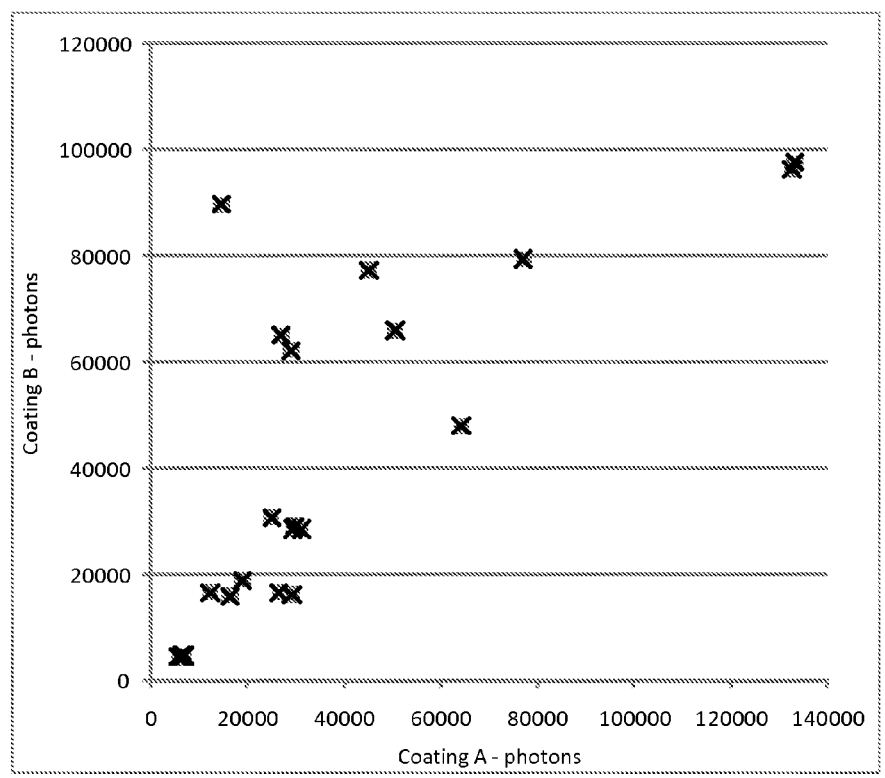
FIG. 7 illustrates numerical values associated with an embodiment of the present invention.
FIG. 8 illustrates a plot of some of the numerical values of FIG. 7.

In order to illustrate the applicability of a processing method such as PCA to a measurement with an apparatus according to an embodiment of the invention, the table in FIG. 7 lists certain measured and calculated values. Bottled drinking water of six different brands and some water from the tap were analysed by taking three samples of each. From each sample, a sample carrier was prepared by immersing in the sample a plate comprising interacting surfaces of six different kinds. The interacting surfaces were all non-specific surfaces (NSS) and are labelled NSS1, NSS2, NSS3, NSS4, NSS5, and NSS6 in the table. The numbers in the first six number columns of the table are photon counts received after introducing excitation in the form of a pulse from an ultraviolet LED onto the corresponding interacting surface. For example, the number 135028 at the top left tells that in the measurement of the first tap water sample, flashing the ultraviolet LED above the interacting surface NSS1 produced 135028 luminescent photons.

FIG. 8 illustrates a test of whether some reasonable analysis could be done of the data by plotting the data points taken from two columns alone: here, the horizontal axis represents the values read from the NSS4 column and the vertical axis represents the corresponding values read from the NSS3 column. If testing the samples on only these two interacting surfaces would suffice for differentiating the samples from each other, the points in FIG. 8 should appear in clear clusters of three. It is easy to see that this is not the case.

Figure 9:
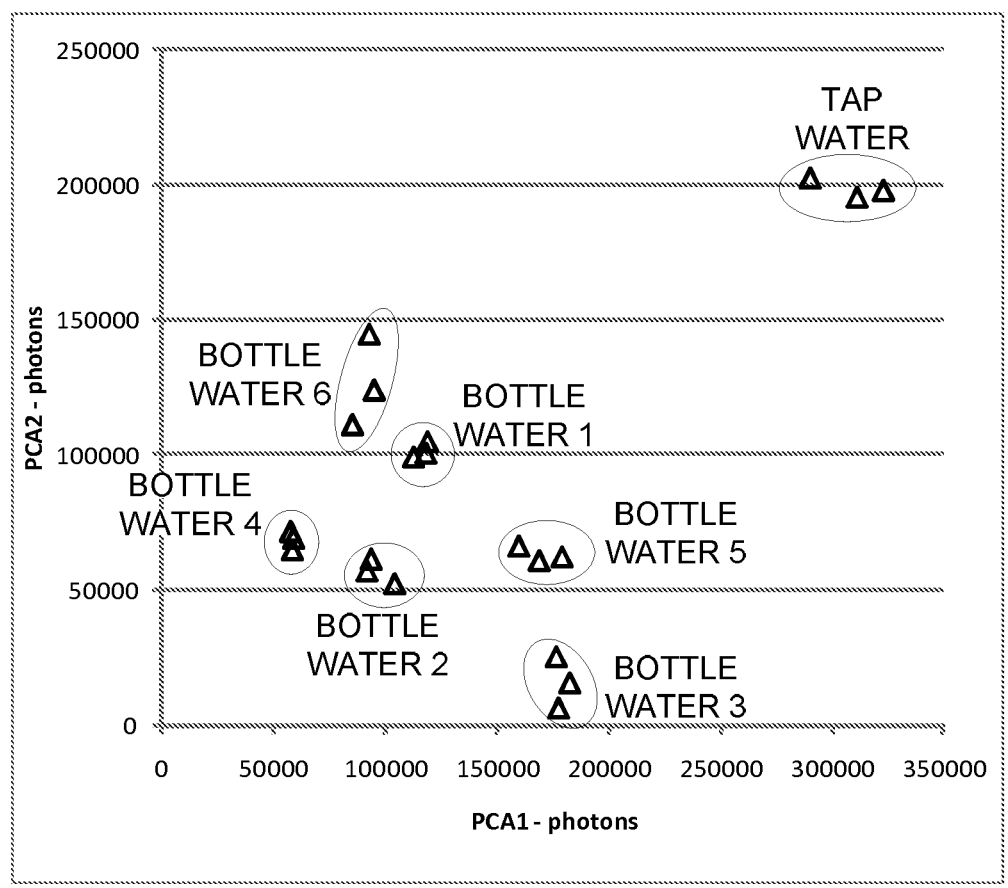
FIG. 9 illustrates a plot of some other numerical values of FIG. 7.

The PCA1 and PCA2 columns in the table of FIG. 7 list the two unnormalized principal components calculated for the six actual data points of the corresponding row. Thus for example the PCA1 and PCA2 values 322909 and 197744 on the topmost number row are the two unnormalized principal components calculated for the six photon counts 135028, 100191, 97515, 133278, 142444, and 197635 obtained for the first tap water sample. FIG. 9 is a plot of the calculated points (PCA1, PCA2) for each row of the table. It is easy to see that these calculated points are neatly clustered in groups of three.

If now an unknown water sample would be given, it could be analysed by using the sample to prepare a similar sample carrier, measuring the photon counts from each of its six interacting surfaces, and calculating the corresponding two unnormalized principal component values or PCA1 and PCA2 values. Whether or not the unknown sample would resemble any of the seven known samples discussed above would be determined by looking, whether its (PCA1, PCA2)-point would reasonably fit in or close to any of the seven ovals illustrated in FIG. 9.

The present invention allows taking unique advantage of the principle of statistical analysis such as PCA, by making "analogue PCA" in the form of simultaneous excitation of a number of interacting surfaces and common detection of the resulting luminescent photons. We may recall that according to an embodiment of the invention, the detecting means are common and can thus detect luminescent photons from a multitude of excited interacting surfaces simultaneously. It should be noted that obtaining the 21×6 numerical values in the NSS1, NSS2, NSS3, NSS4, NSS5, and NSS6 columns of FIG. 7 one by one necessitated making 21×6=126 different measurements, only activating a single ultraviolet LED (or, if there are n identical interacting surfaces, n ultraviolet LEDs) at a time. This number of measurements could be reduced to 21×2=42 by cleverly composing two subgroups of LEDs. Each subgroup would be characterised by which LEDs belong to it, and what intensity would be selected for each LED. Selecting an intensity can be made for example by selecting the electric current to be directed through the corresponding LED, and/or by individually selecting the pulse length in time for each LED in the subgroup. Activating the LEDs of a subgroup would provide appropriate excitation to those interacting surfaces that coincide with LEDs of that subgroup.

If the subgroups are composed correctly, we may assume that the "principal component" photon counts of the PCA1 and PCA2 columns would be obtained by measuring the luminescent response to the activation of the first and second subgroups respectively. Thus in order to analyse an unknown sample only two photon count readings would need to be made, selectively activating one of the two subgroups for each reading as explained above.

Statistical analysis methods such as PCA can produce a single characteristic descriptor value, two characteristic descriptor values (such as the PCA1 and PCA2 values in the table of FIG. 7), or more than two characteristic descriptor values. The more characteristic descriptor values are used, the more accurate description of the original data set is typically obtained. In an analogous fashion, the more subgroups of excitation means are composed, and the resulting photon counts measured, the more accurate conclusions may be drawn about a measured sample resembling some known sample. However, it should be noted that in addition to the improved signal to noise ratio, one major advantage of activating the excitation means in subgroups instead of just one at a time was the resulting reduced number of individual measurements. If the number of subgroups begins to approach the number of different interacting surfaces on the sample carrier, this advantage risks to be lost.

In addition to the method and apparatus embodiments described above the present invention relates to a computer program product used for controlling the operation of the apparatus 200, such as controlling the radiating excitation means 201, detecting means 202 as well as data processing in order to obtain a fingerprint of the sample. The computer program product advantageously comprises machine-readable instructions that, when executed by a processor (such as the master controller 503 in FIG. 5), are configured to cause the processor implement a method comprising:
as a response to an indication of a sample carrier being held in place by a holder, selectively introducing excitation from a plurality of excitation means towards a desired portion of said sample carrier, and
receiving and detecting emission radiation coupled out from a light output window of said sample carrier;
wherein said receiving and detecting is performed commonly to said excitation means by receiving and detecting emission radiation with a common detector from a plurality of different spatially limited portions of said sample carrier.

Additionally the present invention relates to a system, which comprises the apparatus described above and a sample carrier described above, with the plurality of sample wells and with integrated optical functionality.

The present invention has been explained above with reference to the aforementioned embodiments, and several advantages of the invention have been demonstrated. It is clear that the present invention is not only restricted to these embodiments, but comprises all possible embodiments within the spirit and scope of the inventive thought and the following patent claims.

The present invention offers clear advantages. For example virtually any liquid can be "profiled". In addition the technology works very well both in comparative analysis and detection of differences in samples which suggests that the natural applications are in authenticity and safety. The measurement procedure itself may be a simple dip-and-read type test.

The time-resolved fluorescence (TRF), the sensing technology used by the embodiments of the present invention, gives sensitivity down to attomolar levels (sensing to approximately $1*10^{-15}$ concentrations) which can be compared to most electronic nose technologies based on semiconductor technologies which can achieve $1*10^{-6}$ concentrations, i.e. 1/1,000,000,000 times less sensitive than the embodiments of the present invention.

The present invention employs devices with specific and non-specific surfaces. The main difference between specific and non-specific sensing is that a non-specific approach can detect differences in any unknown sample—whether it contains the predicted substances or not. If e.g. 49 specific sensors that can measure individual properties from 1-1000 are combined, this results in a maximum of 49.000 different combinations for the analyte. With the non-specific approach utilized by the embodiments of the present invention, the result of every single non-specific sensor yield information that can be used together with the other sensors, means that 49 non-specific sensors read from 0-1000 mean that the maximum combinations are $1*10^{149}$. The combination of non-specific sensing with time-resolved fluorometry means almost single-molecule sensitivity with virtually endless combinations all embedded in a simple disposable test slide or device.

The invention claimed is:

1. A method for examining optically a sample, carried in a plurality of wells, the method comprising:
receiving a sample carrier in a holder and holding said sample carrier in place;
selectively introducing excitation from an excitation means subgroup, where the excitation means subgroup comprises at least two excitation means, towards at least two of the wells of the sample carrier, and wherein each of the two wells comprising:
differently coated or modified surfaces each forming a differently behaving non-specific interacting surface;
a luminophore label;
the sample, and wherein said surfaces are configured to:
interact with the sample but not with the luminophore label;
interact with the luminophore label but not with the sample; and/or
interact with a combination of the sample and the luminophore label; and receiving and detecting emission radiation coupled out from the at least two of the wells of the sample carrier;
wherein said receiving and detecting is performed commonly to the excitation means subgroup by receiving and detecting emission radiation with a common detector from a plurality of different spatially limited portions of the sample carrier.

2. The method according to claim 1, wherein the step of selectively introducing excitation comprises switching on a predetermined subgroup of available radiating excitation means for radiating excitation radiation.

3. The method according to claim 2, wherein a number of predetermined subgroups of the available radiating excitation means are switched on in sequence, each subgroup comprising a number of radiating excitation means that is at least one and at most as many as there are available radiating excitation means.

4. The method according to claim 2, wherein said excitation is introduced in pulses, and said emission radiation is detected during a time interval in a range of 100 µs to 1000 µs following an excitation pulse.

5. The method according to claim 2, wherein at least one of wavelength, intensity, polarization, or exposure of at least one excitation means of the excitation means subgroup is adjusted independently from at least one other excitation means of said excitation means subgroup.

6. The method according to claim 5, further comprising:
executing a sequence of excitation pulses, each excitation pulse implementing a characteristic spatially limited pattern of excitation,
receiving and detecting emission radiation as a response to each excitation pulse, and
storing information that relates the executed sequence of excitation pulses to the received and detected emission radiation as a fingerprint of a sample held by a particular sample carrier.

7. The method according to claim 1, wherein at least one of wavelength, intensity, polarization, or exposure of at least one excitation means of the excitation means subgroup is adjusted independently from at least one other excitation means of said excitation means subgroup.

8. The method according to claim 1, further comprising:
executing a sequence of excitation pulses, each excitation pulse implementing a characteristic spatially limited pattern of excitation,
receiving and detecting emission radiation as a response to each excitation pulse, and
storing information that relates the executed sequence of excitation pulses to the received and detected emission radiation as a fingerprint of a sample held by a particular sample carrier.

9. A method according to claim 1, wherein said excitation is introduced in pulses, and said emission radiation is detected during a time interval in a range of 100 µs to 1000 µs following an excitation pulse.

10. An apparatus for examining optically a sample, carried in a plurality of wells, the apparatus comprising:
a holder adapted to receive and hold in place a sample carrier;
an excitation means subgroup adapted to selectively introduce excitation towards at least two of the wells of the sample carrier held in place by the holder, where the excitation means subgroup comprises at least two excitation means, and wherein each of the two wells comprising:
differently coated or modified surfaces each forming a differently behaving non-specific interacting surface;
a luminophore label;
the sample, and wherein said surfaces are configured to:
interact with the sample but not with the luminophore label;
interact with the luminophore label but not with the sample; and/or
interact with a combination of the sample and the luminophore label; and
detecting means for receiving and detecting emission radiation coupled out from the at least two of the wells of said sample carrier held in place by said holder;
wherein the detecting means is common to the excitation means subgroup and is configured to receive emission radiation from a plurality of different spatially limited portions of the sample carrier held in place by the holder.

11. The apparatus according to claim 10, wherein said excitation means comprise radiating excitation means that comprise a regular array of individually controllable radiation sources configured to correspond with a regular array of sample spots or wells in a sample carrier held in place by said holder.

12. The apparatus according to claim 11, wherein the radiating excitation means comprise at least one of the following: light-emitting diodes, laser sources, output ends of optical fibers.

13. The apparatus according to claim 10, further comprising an excitation controller configured to switch on the excitation means in subgroups, each subgroup comprising a number of excitation means that is at least one and at most as many as there are excitation means in the apparatus.

14. The apparatus according to claim 10, wherein the excitation means have a wavelength, and a wavelength of at least one excitation means differs from the wavelength of another excitation means.

15. The apparatus according to claim 10, wherein at least one excitation means has a controllable wavelength.

16. The apparatus according to claim 10, wherein the excitation means and the detecting means are stationary.

17. The apparatus according to claim 10, wherein the detecting means comprise an emission radiation input window configured to match an emission radiation output window defined by a sample carrier held in place by said holder.

18. The apparatus according to claim 10, wherein at least one of wavelength, intensity, polarization, or exposure of at least one excitation means of the excitation means subgroup is configured to be adjustable independently from at least one other excitation means of said excitation means subgroup.

19. The apparatus according to claim 10, further comprising an identification reader configured to read an identifier of a sample carrier held in place by said holder.

20. A computer program product comprising machine-readable instructions that, when executed by a processor, are configured to cause the processor to implement a method, the method comprising:
as a response to an indication of a sample carrier being held in place by a holder, selectively introducing excitation from an excitation means subgroup towards at least two of the wells of the sample carrier, where said excitation means subgroup comprises at least two excitation means, and wherein each of the two wells comprising:
differently coated or modified surfaces each forming a differently behaving non-specific interacting surface;
a luminophore label;
the sample, and wherein said surfaces are configured to:
interact with the sample but not with the luminophore label;

interact with the luminophore label but not with the sample; and/or interact with a combination of the sample and the luminophore label; and receiving and detecting emission radiation coupled out from said at least two of the wells of said sample carrier;

wherein said receiving and detecting is performed commonly to said excitation means subgroup by receiving and detecting emission radiation with a common detector from a plurality of different spatially limited portions of said sample carrier.

21. An apparatus for optically detecting a fingerprint of luminescent intensities of a sample, the apparatus comprising:

a holder adapted to receive and hold in place a sample carrier, the sample carrier having the sample carried in a plurality of wells;

an excitation means subgroup adapted to selectively introduce excitation towards at least a first and second well of the plurality of wells of the sample carrier held in place by the holder, wherein the excitation means subgroup comprises at least a first and second excitation means, the first excitation means subgroup adapted to radiate excitation radiation at a first wavelength to at least a portion of the first well of the sample carrier and the second excitation means subgroup adapted to radiate excitation radiation at a second wavelength to at least a portion of the second well of the sample carrier, and wherein each of the at least first and second wells comprising:

differently coated or modified surfaces each forming a differently behaving non-specific interacting surface;

a luminophore label; and the sample;

wherein said differently coated or modified surfaces are configured to:

interact with the sample but not with the luminophore label;

interact with the luminophore label but not with the sample; and/or interact with a combination of the sample and the luminophore label; and detecting means for receiving and detecting emission radiation coupled out from the at least first and second wells of the plurality of wells of the sample carrier held in place by the holder;

wherein the detecting means is common to the excitation means subgroup and is configured to receive emission radiation from a plurality of different spatially limited portions of the sample carrier held in place by the holder.

* * * * *